United States Patent [19]

Erpenbach et al.

[11] Patent Number: 4,717,454
[45] Date of Patent: Jan. 5, 1988

[54] PROCESS FOR REMOVING ACETONE FROM REACTION MIXTURES OF CARBONYLATION REACTIONS

[75] Inventors: Heinz Erpenbach, Cologne; Klaus Gehrmann; Peter Hörstermann, both of Erftstadt; Georg Kohl, Hürth, all of Fed. Rep. of Germany

[73] Assignee: Hoechst Aktiengesellschaft, Werk Knapsack, Fed. Rep. of Germany

[21] Appl. No.: 774,384

[22] Filed: Sep. 10, 1985

Related U.S. Application Data

[63] Continuation of Ser. No. 442,105, Nov. 16, 1982, abandoned.

[30] Foreign Application Priority Data

Dec. 11, 1981 [DE] Fed. Rep. of Germany ....... 3149094

[51] Int. Cl.$^4$ ............................................. B01D 5/00
[52] U.S. Cl. ...................................... 203/29; 203/49; 203/75; 203/77; 203/78; 203/80; 203/82; 203/84; 203/DIG. 6; 568/411
[58] Field of Search ....................... 203/78, 71, 74, 73, 203/77, 80, 81, 29, 49, 75, 82, 84, DIG. 6; 568/411, 387, 410

[56] References Cited

U.S. PATENT DOCUMENTS

| 2,704,271 | 3/1955 | Harrison et al. | 203/75 |
| 3,153,068 | 10/1964 | Porter et al. | 568/388 |
| 3,215,745 | 11/1965 | Frank | 568/410 |
| 3,686,078 | 8/1972 | Hauptmann et al. | 203/75 |
| 4,252,741 | 2/1981 | Porcelli et al. | 568/484 |
| 4,252,748 | 2/1981 | Hoch et al. | 568/387 |
| 4,302,611 | 11/1981 | Porcelli | 568/484 |
| 4,381,221 | 4/1983 | Isshiki et al. | 203/61 |
| 4,418,196 | 11/1983 | Nakahara et al. | 546/242 |
| 4,444,624 | 4/1984 | Erpenbach et al. | 568/387 |
| 4,536,581 | 8/1985 | Cantatore et al. | 546/242 |

FOREIGN PATENT DOCUMENTS

| 0074506 | 3/1983 | European Pat. Off. | 568/411 |
| 0055509 | 5/1979 | Japan | 568/410 |
| 0640581 | 7/1950 | United Kingdom | 568/410 |
| 0726080 | 4/1980 | U.S.S.R. | 568/410 |

OTHER PUBLICATIONS

Fieser et al, "Organische Chemie", 1963, pp. 551 & 552.
Cope et al, "Organic Reactions", vol. 16, p. 19.

Primary Examiner—S. Leon Bashore
Assistant Examiner—V. Manoharan

[57] ABSTRACT

A process for removing by product acetone from reaction mixtures obtained by reacting methyl acetate and/or dimethylether with carbon monoxide at elevated temperatures to obtain acetic anhydride in the presence of a catalyst system consisting essentially of carbonyl complexes of noble metals belonging to group VIII of the Periodic System of the elements, acetic acid, an organophosphorus or organonitrogen compound, and methyl iodide whereby the acetone obtained as a by-product during the reaction is subjected to condensation at temperatures of 50° to 250° C., under pressures of 0.01 to 150 bars and at a molar ratio as above defined for the catalyst system constituent of 1:(25–500):(10–100):(-15–150) so as to obtain predominantly higher-boiling secondary products to be distillatively separated in a successive distillation zone together with volatile constituents of the catalyst system.

5 Claims, 1 Drawing Figure

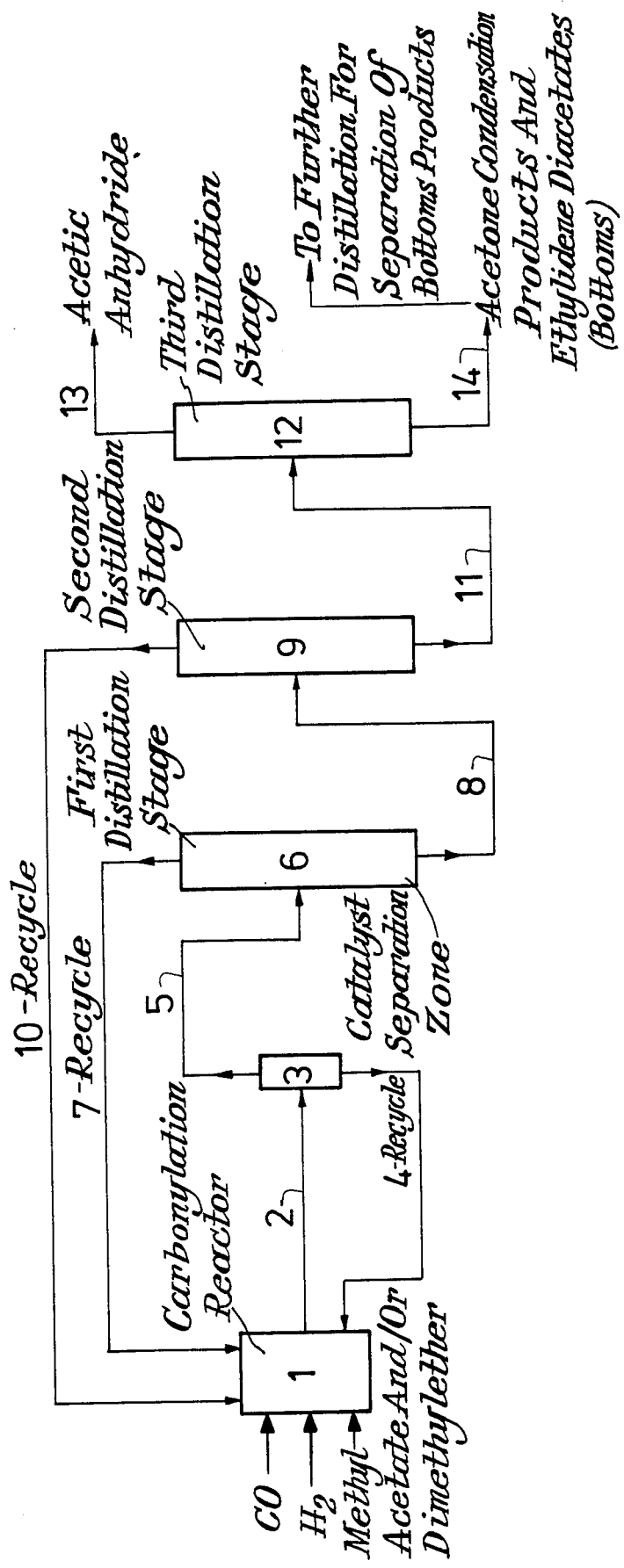

PROCESS FOR REMOVING ACETONE FROM REACTION MIXTURES OF CARBONYLATION REACTIONS

This is a continuation of our copending application, Ser. No. 442,105 filed Nov. 16, 1982, now abandoned.

The present invention relates to a process for removing acetone from reaction mixtures which are obtained by reacting methyl acetate and/or dimethylether with carbon monoxide and optionally hydrogen at elevated temperatures to obtain acetic anhydride and optionally ethylidene diacetate in the presence of a catalyst system consisting essentially of carbonyl complexes of noble metals belonging to group VIII of the Periodic System of the elements, acetic acid, an organophosphorus or organonitrogen compound and methyl iodide in a molar ratio of 1:(25–600):(10–300):(10–300) and optionally compounds of carbonyl-yielding common metals, such as those disclosed e.g. in DE-OS Nos. 24 50 965; 28 36 084; 29 39 839 and 29 41 232.

Carbonylation reactions of the kind just described produce reaction mixtures which contain non-volatile catalyst constituents consisting primarily of compounds of a noble metal of group VIII of the Periodic System and of the organophosphorus or organonitrogen compounds used as promoters, together with volatile constituents consisting of acetic anhydride, ethylidene diacetate, acetic acid and methyl iodide as well as of unreacted methyl acetate and optionally dimethylether. In addition to this, the reaction mixture contains minor proportions of acetone which is obtained as an undesirable by-product during the carbonylation. In continuously operated carbonylation units, the non-volatile catalyst system is generally separated first from the volatile constituents. Next, the volatile constituents are subjected to further distillative separation and the low boilers comprising methyl iodide and unreacted methyl acetate and/or dimethylether are distilled off overhead.

As a result of the fact that acetone and methyl acetate have boiling points which differ but slightly from one another (methyl acetate: 57° C.; acetone: 56° C.), the low boilers so distilled off also contain the acetone formed as a by-product. Since the low boilers distilled off are completely recycled into the reactor, it is only natural that acetone commences concentrating in the reaction product or low boiler mixture. This is undesirable, however, as higher acetone concentrations have been found during the reaction adversely to affect the activity of the catalyst and also the formation of by-products.

DE-OS No. 29 52 516 (=U.S. Pat. No. 4,252,748) discloses a process for separating acetone from the volatile constituents of a reaction mixture which is obtained by subjecting methyl acetate to reaction with carbon monoxide and hydrogen in the presence of a noble metal of group VIII of the Periodic System of the elements and methyl iodide, which comprises: establishing a molar ratio of acetone to methyl iodide of at least 1:10 in the mixture of volatile constituents by introducing acetone into the carbonylation zone; subjecting the mixture of volatile constituents to fractional distillation so as to separate practically all of the methyl iodide and a portion of the acetone and methyl acetate as distillate, the quantity of acetone separated corresponding practically to the quantity used in the reaction; distilling off residual acetone and methyl acetate from the distillation residue, and separating the acetone from the methyl acetate/acetone-mixture.

As described in U.S. Pat. No. 2,704,271, the acetone formed during the reaction is separated from the acetone/methylacetate-mixture by azeotropic distillation with $C_5$-hydrocarbons, extraction of the resulting acetone/$C_5$-hydrocarbon-mixture with water, and fractionation of the acetone from the water phase.

This acetone separation process requires high capital investment and expenditure of energy for distillation.

The present process now provides a process which is easier to carry out and permits the concentration of acetone in the reaction mixture of a carbonylation reaction to be avoided.

We have now unexpectedly found that the acetone concentration in the separated low boiler mixture increases up to about 5 weight % and then stagnates subject to the provision of certain reaction conditions. Under the reaction and work up conditions selected in accordance with this invention, freshly formed acetone undergoes reaction (condensation) to secondary products containing 6 to 12 carbon atoms. These secondary products have boiling points which on the one hand make it possible for them to be separated together with further distillable material from the non-volatile catalyst system, and on the other hand make it possible for them to be retained together with acetic acid and formed acetic anhydride as base (i.e. bottoms) product in the separating zone, after separation of the low boilers consisting of methyl iodide and methyl acetate. In this manner it is ensured that the acetone secondary products which strongly impair the catalyst efficiency and initiate, in the reaction zone, further condensation reactions, are neither recycled together with non-volatile constituents of the catalyst system nor with the methyl iodide and methyl acetate low boilers into the reactor. In other words, these products are definitely prevented from accumulating in the reactor. After distillative separation of acetic acid and acetic anhydride, the acetone secondary products are retained in the base portion of the anhydride column from which they can be removed.

The acetone condensation depends primarily on the quantitative ratio of the reactants in the reaction zone and in the catalyst separating zone. It has been found that freshly formed acetone which is continuously obtained during the reaction undergoes complete condensation upon establishment of a molar ratio of noble metal to acetic acid to organonitrogen and/or organophosphorus compound to methyl iodide of 1:(25–500):(10–100):(15–150), and a stationary acetone content of 5 weight % acetone in the low boiler mixture. In the event of the low boiler mixture containing initially less acetone, the acetone is found to concentrate therein up to about 5 weight % prior to any significant formation of condensation products. In the event of a low boiler mixture with more than 5 weight % acetone being introduced into the reaction zone, the acetone content becomes first decreased to and then remains at 5 weight % acetone in the low boiler mixture; this is accompanied by an intensified formation of condensation products.

The process of the present invention comprises more particularly: subjecting the acetone obtained as a by-product during the reaction to condensation at temperatures of 50° to 250° C., under pressures of 0.01 to 150 bars and at a molar ratio as above defined of 1:(25–500):(10–100):(15–150) so as to obtain predominantly higher-boiling secondary products, distillatively separating these latter together with volatile constituents of the reaction mixture from the non-volatile constituents of the catalyst system, and separating resulting distillate in a successive distilling zone into a low boiler mixture consisting of methyl iodide, unreacted methyl acetate and/or dimethylether and residual acetone, and into a base (i.e. bottoms) product consisting of acetic acid, acetic anhydride and optionally ethylidene diacetate, and the acetone secondary products.

Preferred optional features of the present invention provide:

(a) for the volatile constituents of the reaction mixture to be distillatively separated from the non-volatile constituents of the catalyst system at temperatures of 50° to 170° C. under pressures of 0.01 to 3 bars;

(b) for the volatile constituents of the reaction mixture to be distillatively separated from the non-volatile constituents of the catalyst system in the presence of carbon monoxide and optionally hydrogen;

(c) for the base product coming from the distilling zone to be successively freed distillatively from acetic acid, acetic anhydride and optionally ethylene diacetate.

BRIEF DESCRIPTION OF THE DRAWING

The invention will now be described in greater detail with reference to the accompanying flow scheme.

Methyl acetate and/or dimethylether are placed in a carbonylation reactor 1 and reacted therein with carbon monoxide and optionally hydrogen in the presence of a catalyst system comprised of carbonyl complexes of noble metals of group VIII of the Periodic System of the elements, acetic acid, an organophosphorus or organonitrogen compound and methyl iodide in a molar ratio of 1:(25-500):(10-100):(15-150) at temperatures of 150° to 200° C. under pressures of 25 to 150 bars. The reaction mixture is introduced through line 2 into catalyst separation zone 3, in which distillable matter is separated under a pressure of 0.1 to 2 bars and at temperatures of 75° to 170° C. from the non-volatile catalyst system, and this latter is recycled via line 4 to the reactor. The volatile constituents are introduced through line 5 into a first distilling stage 6, in which the low boilers comprised of methyl iodide, unreacted methyl acetate and acetone are separated overhead. This head (i.e. overhead) product is recycled via line 7 to reactor 1. The base product, which is a mixture of acetic acid, acetic anhydride and ethlidene diacetate and which also contains high-boiling condensation products of acetone, is introduced through line 8 into a second distilling stage 9, in which acetic acid is separated overhead and recycled through line 10 to reactor 1. The base product is introduced through line 11 into a third distilling stage 12, in which produced acetic anhydride is obtained as head product through line 13. The base product is composed of ethylidene diacetate and acetone condensation products and is removed through line 14. It is possible for the ethylidene diacetate to be distillatively separated in a further distilling zone (not shown in the drawing); (bp 169° C. under a pressure of 1013 millibars; 111° C. under a pressure of 150 millibars).

The process just described offers the advantage that acetone which is an undesirable by-product concentrates in the low boiler mixture to an extent of 5 weight % only. Acetone which is formed in excess of 5 weight % undergoes condensation under the conditions of this invention to secondary products which are removed from the system through the base portion of the third distilling stage 12 without additional expense for distillation.

EXAMPLE 1

The carbonylation was effected at a temperature of 185° C. under a CO-partial pressure of 50 bars. The total pressure inside reactor 1 increased up to 70 bars. The reaction mixture contained Rh-complex, acetic acid, methyltributyl phosphonium iodide, methyl iodide and methyl acetate in the molar ratio of 1:152:37:68:340. 23,450 g/h reaction mixture was taken from reactor 1 and separated in catalyst separating stage 3 under a pressure of 150 millibars, at 95° C. and while adding 20 l/h synthesis gas ($CO:H_2=1:1$) into 6900 g/h catalyst system and 16,550 g/h volatile constituents. The volatile constituents were separated in first distilling stage 6 into 6137 g/h of a mixture of acetic acid and acetic anhydride, which was obtained as base product, and 10,413 g/h of a low boiler fraction of methyl iodide and methyl acetate which was distilled off overhead. The catalyst system and low boiler fraction were recycled through lines 4 and 7, respectively, to reactor 1.

At the time of starting the experiment, the low boiler mixture was free from acetone. The acetone concentration, determined in respect of time, is indicated in the following Table.

The base product coming from the first distilling stage 6 was introduced into the second distilling stage 9 and 2636 g/h acetic acid was distilled off therein and recycled through line 10 to the reactor. 3501 g/h acetic anhydride was retained in the base portion together with minor proportions of ethylidene diacetate and acetone condensation products. The distillation in the third distilling stage 12 gave 3450 g/h acetic anhydride as head product and 51 g/h residue containing little acetic anhydride together with ethylidene diacetate and condensation products of acetone. At the time of starting the experiment, this base product could not be found to contain condensation products. The concentration of these secondary products of acetone in the base portion of the third distillng stage 12, determined in respect of time, is shown in the following Table.

| Time (days) | Acetone concentration in stream 7 wgt % | Concentration of acetone secondary products in stream 14 wgt % |
| --- | --- | --- |
| 0 | 0 | 0 |
| 10 | 2.0 | 0.02 |
| 20 | 3.8 | 0.2 |
| 30 | 4.5 | 1.1 |
| 40 | 5.0 | 2.4 |
| 50 | 5.0 | 2.4 |
| 60 | 5.0 | 2.4 |

EXAMPLE 2

The experiment was carried out as in Example 1 save that at the time of starting the experiment the low boiler mixture was admixed with acetone so as to establish an acetone concentration of 9 weight %. The acetone concentration in the low boiler mixture and the concentration of the acetone condensation products in the base portion of the third distilling zone, determined in respect of time, are indicated in the following Table.

| Time (days) | Acetone concentration in stream 7 wgt % | Concentration of acetone secondary products in stream 14 wgt % |
| --- | --- | --- |
| 0 | 9.0 | — |
| 10 | 6.5 | 4.5 |
| 20 | 5.3 | 3.2 |
| 30 | 5.0 | 2.4 |
| 40 | 5.0 | 2.4 |
| 50 | 5.0 | 2.4 |

EXAMPLE 3

The experiment was effected as in Example 1 but the pressure was increased to 1.2 bars and the temperature to 145° C. in catalyst separating stage 3. At the time of starting the experiment, acetone was added to the low boiler mixture so as to establish a concentration of 5 weight %. The acetone concentration in the low boiler mixture and concetration of the acetone secondary products in the base portion of the third distilling stage 12, determined in respect of time, are indicated in the following Table.

| Time (days) | Acetone concentration in stream 7 wgt % | Concentration of acetone secondary products in stream 14 wgt % |
| --- | --- | --- |
| 0 | 5.0 | — |
| 10 | 5.0 | 2.4 |
| 20 | 5.0 | 2.4 |
| 30 | 5.0 | 2.4 |

EXAMPLE 4

The carbonylation was effected at a temperature of 185° C. and under a total pressure of 110 bars. The methyl acetate used as feed material in the preceding Examples was replaced by dimethylether. The reaction mixture contained Rh-complex, acetic acid, methyltributyl phosphonium iodide, methyl iodide, methyl acetate and dimethylether in the molar ration of 1:152:37:68:287:53. 23,149 g/h reaction mixture was taken from reactor 1 and separated in catalyst separating stage 3 under a pressure of 150 millibars, at 95° C. and while adding 20 l/h synthesis gas (CO:$H_2$=1:1) into 6900 g/h catalyst system and 16,249 g/h volatile constituents. The volatile constituents were separated in first distilling stage 6 into 5836 g/h of a mixture of acetic acid and acetic anhydride which was the base product, and 10,413 g/h of a low boiler fraction of methyl iodide, methyl acetate and dimethylether which distilled off overhead. The catalyst system and low boiler fraction were recycled through lines 4 and 7, respectively, to reactor 1.

At the time of starting the experiment, the low boiler mixture was free from acetone. The acetone concentration in this mixture, determined in respect of time, is indicated in the following Table.

In the second distilling stage 9, 2636 g/h acetic acid was distilled off from the base product obtained in the first distilling stage 6 and recycled through line 10 to the reactor. 3200 g/h acetic anhydride was retained in the base portion together with minor proportions of ethylidene diacetate and condensation products of acetone. The distillation in the last, i.e. third distilling stage 12 gave 3150 g/h acetic anhydride as head product and 50 g/h of a residue which contained a minor proportion of acetic anhydride together with the ethylidene diacetate and acetone condensation products. At the time of starting the experiment, this base product not be found to contain condensation products. The concentration of these acetone secondary products in the third distilling stage 12, determined in respect of time, is indicated in the following Table.

| Time (days) | Acetone concentration in stream 7 wgt % | Concentration of acetone secondary products in stream 14 wgt % |
| --- | --- | --- |
| 0 | 0 | 0 |
| 10 | 1.9 | 0.02 |
| 20 | 3.7 | 0.2 |
| 30 | 4.5 | 1.0 |
| 40 | 5.0 | 2.4 |
| 50 | 5.0 | 2.4 |

We claim:

1. In a process for removing byproduct acetone from reaction mixtures obtained from the carbonylation of a starting material, wherein the starting material is methyl acetate, dimethyl ether, or mixtures thereof, in the presence of a catalyst system consisting essentially of:

a carbonyl complex of a noble metal of group VIII of the Periodic System of the elements, acetic acid, an organophosphorus or organonitrogen compound, and methyl iodide in a molar ratio of 1:(25–600):(10–300):(10–300), the improvement comprising:

(a) subjecting the acetone obtained as a by-product during the reaction to condensation at temperatures of 50° to 250° C., under pressures of 0.01 to 150 bars and at a molar ratio as above defined of 1:(25–500):(10–100):(15–150), and as a result of said conditions acetone condensation products containing 6 to 12 carbon atoms are produced from the acetone;

(b) conveying the contents of the carbonylation zone to a catalyst separation zone and separating the volatile constituents of said contents from the non-volatile constituents of the catalyst system;

(c) conveying the said volatile constituents obtained in said step (b) to a first distillation zone to provide a lower-boiling overhead mixture containing methyl iodide, unreacted starting material, and a residual acetone content of about 5 weight % acetone, and a higher-boiling bottoms product containing acetic acid, acetic anhydride, ethylidene diacetate, and the acetone condensation products; and recycling said overhead mixture to the carbonylation zone; whereby the acetone content of said overhead mixture is reduced due to the content of acetone condensation products in the bottoms product.

2. A process as claimed in claim 1, wherein the volatile constituents of the reaction mixture are separated from the non-volatile constituents of the catalyst system at temperatures of 50° to 170° C. under pressures of 0.01 to 3 bars.

3. A process as claimed in claim 1, wherein the volatile constituents of the reaction mixture are separated from the non-volatile constituents of the catalyst system in the presence of a gas, wherein the gas is carbon monoxide or a mixture of hydrogen and carbon monoxide.

4. A process as claimed in claim 1, wherein the bottoms product of the first distillation zone is separated in a second distillation zone into acetic acid and a second bottoms product containing acetic anhydride, ethylidene diacetate and the acetone condensation products.

5. A process as claimed in claim 4, wherein said second bottoms product is passed to a third distillation zone and acetic anhydride is recovered as overhead product and ethylidene diacetate is recovered as the bottoms product of the third distillation zone and separated from the acetone condensation product in a further distillation zone.

* * * * *